US006186761B1

(12) United States Patent
Petkow et al.

(10) Patent No.: US 6,186,761 B1
(45) Date of Patent: *Feb. 13, 2001

(54) DENTAL INJECTION MOLDING SYSTEM

(75) Inventors: Lothar Petkow; Wolf Parisius, both of Grafton; A. A. Robertson, Toronto, all of (CA)

(73) Assignee: GC America, Inc., Tokkyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/025,906

(22) Filed: Feb. 19, 1998

Related U.S. Application Data

(60) Provisional application No. 60/038,630, filed on Feb. 19, 1997.

(51) Int. Cl.[7] .................................................... A61C 13/20

(52) U.S. Cl. .............................. 425/178; 264/17; 264/19; 264/478; 249/54; 425/174.4; 425/567; 425/DIG. 11

(58) Field of Search ................................ 264/16, 17, 19, 264/478; 249/54, 55; 425/174, 174.4, 562, DIG. 11, 178, 542

(56) References Cited

U.S. PATENT DOCUMENTS

| | | |
|---|---|---|
| 723,275 | 3/1903 | Hood . |
| 1,533,625 | 4/1925 | Williams . |
| 1,875,660 | 9/1932 | Rodin et al. . |
| 2,192,902 | 3/1940 | Erdle . |
| 2,195,452 | 4/1940 | Erdle . |
| 2,341,991 | 2/1944 | Jackson . |
| 2,442,847 | 6/1948 | Galley . |
| 2,543,110 | 2/1951 | Hordes . |
| 2,576,224 | 11/1951 | Hordes . |
| 2,887,717 | 5/1959 | Smith . |
| 3,355,526 | 11/1967 | Molnar . |
| 4,265,669 | 5/1981 | Starling et al. ...................... 106/73.4 |
| 4,359,435 | 11/1982 | Kogure ................................ 264/40.5 |
| 4,735,760 | 4/1988 | Kumazaki .......................... 264/40.5 |
| 5,023,039 | 6/1991 | Sorensen .......................... 264/297.2 |
| 5,043,129 | 8/1991 | Sorensen .......................... 264/297.2 |
| 5,044,925 | 9/1991 | Watanabe .............................. 425/542 |
| 5,104,591 | 4/1992 | Masuhara et al. ..................... 264/16 |
| 5,175,008 | 12/1992 | Ueno .................................... 425/178 |
| 5,302,104 | 4/1994 | Ueda .................................... 425/178 |
| 5,324,186 | 6/1994 | Bakanowski ......................... 425/116 |
| 5,480,606 | 1/1996 | Julian ................................ 264/328.7 |

OTHER PUBLICATIONS

781 "Flexural Properties of Compression an–and Injection–molded Denture Resins," Powers and El Sheikh, Houston Biomaterials Research Center, UT–Houston Dental Branch, Houston, Texas, USA.

"Cytotoxicity of Denture Base Resins," Sheridan et al., vol. 10, No. 1, 1997, The International Journal of Prosthodontics, pp. 73–77.

"Dimensional Changes of Relined Denture Bases with Heat–cured, Microwave–activated, Autopolymerizing, and Visible Light–cured Resins. A Laboratory Study," Sadamori et al., Australian Dental Journal 1995;40(5), pp. 322–326.

(List continued on next page.)

Primary Examiner—Jan H. Silbaugh
Assistant Examiner—Stefan Staicovici
(74) Attorney, Agent, or Firm—Gardner, Carton & Douglas (57) ABSTRACT

The invention includes a system and method for making injection molded dental appliance apparatuses having an injector module removably attached to a dental flask, a press and a controlled compression apparatus, wherein the press and compression apparatus introduce pressure into the dental flask and the injector module, which pressure may or may not be maintained during curing of the appliance. The invention also includes a system for dispensing dental appliance chemicals having at least one chemical dispensing apparatus and a mixing container; whereby a separate dispensing apparatus is used for each chemical and the chemicals are dispensed and mixed in the same container.

12 Claims, 6 Drawing Sheets

OTHER PUBLICATIONS

"An Evaluation of Microwave–Polymerized Resin Bases for Removable Partial Dentures." Ling Loh et al., Journal of Prosthodontics, vol. 5, No. 4, Dec. 1996, pp. 259–265.

"Color Stability: Denture Base Resins Processedd With The Microwave Method," May et al, The Journal of Prosthetic Dentistry, Dec. 1996, pp. 581–589.

"Effect of Plyethylene Fiber Reinforcement on the Strength of Denture Base Resins Polymerized by Microwave Energy," Williamson et al., The Journal of Prosthetic Dentistry, Dec. 1994, pp. 635–638.

"Denture Base Resins: Comparison Study of Color Stability," May et al., Department of Prosthodontics, School of Dentistry, University of Michigan, Ann Arbor, Michigan, Jul. 1992, vol. 68, No. 1, pp. 78–82.

"The Dimensional Accuracy of Rectangular Acrylic Resin Specimens Cured by Three Denture Base Processing Methods," Salim et al., Hiroshima University School of Dentistry, Hiroshima, Japan, The Journal of Prosthetic Dentistry, vol. 67, No. 6, Jun. 1992, pp. 879–881.

"Adaptation of Acrylic Resin Dentures as Influenced by the Acitvation Mode of Polymerization," Takamata et al., JADA, vol. 119, Aug. 1989, pp. 271–276.

DENTAL INJECTION MOLDING SYSTEM

CROSS-REFERENCED TO RELATED APPLICATIONS

This Application claims the benefit of pending U.S. Provisional Application No. 60/038,630, filed on Feb. 19, 1997.

FIELD OF THE INVENTION

This invention relates to a molding system and method for making injection molded dental appliances such as dentures, retainers, prostheses and similar appliances. The invention also relates to a means for dispensing materials which may limit operator exposure to harmful chemicals.

SCOPE OF THE PRIOR ART

Conventional molded dental appliances and methods of making them are widely practiced by dental laboratories. Most molded dental appliances are constructed in a dental flask containing a mold, also called an investment, of the appliance to be formed. The investment is made of plaster or other investment material and is molded around a wax model of the desired appliance, a wax-up, which is embedded in the dental flask. The wax-up may include items such as retainer wires or artificial teeth. Once the investment has hardened, the wax is removed from the dental flask, creating a cavity in the investment of the shape of the desired appliance. The uncured appliance material is then introduced by hand or by conventional injection methods. In conventional methods of packing, approximately three to four tons of force is required in order to squeeze out excess appliance material. After packing, the material is cured in the flask by conventional means such as by conduction heating, thereby forming a dental appliance of the desired shape.

The use of conventional molding systems and methods poses several problems for the practitioner. Often, too much material is added to the investment cavity, resulting in overpacking of the flask. Also, the high pressures can cause distortion of metal frameworks. In addition, when applied to partial dentures, tooth movement frequently occurs, requiring time-consuming reconstruction. Additionally, the material may undergo shrinkage during curing. Overpacking, excess pressure and shrinkage can all result in inaccurately dimensioned dental appliances. In addition, opening and subsequent addition or subtraction of material to the dental flask can cause a variety of significant problems, including but not limited to nonuniform or incomplete curing, the entrapment of air bubbles within the appliance, dislodging of embedded items such as teeth or retaining wires, premature appliance fractures (due to nonuniform preparation of materials), and inaccurately dimensioned appliances.

In addition to the problems disclosed above, conventional methods of mixing the materials may expose the operator to potentially harmful fumes and chemicals. For instance, many dental appliances are created using resins, such as acrylic, urethane or epoxy resins. A number of these resins are currently believed to pose a risk of cancer to exposed persons, and all may be harmful if absorbed through the skin or lungs or ingested, or if fumes emitted from the resins are inhaled. For example, in a conventional acrylic resin preparation of the type generally used in dentistry, the resin material is prepared on a benchtop by combining a fine, loose powder polymer with a liquid monomer and mixing by hand with a small stick or spatula until uniform. The polymer powder readily disperses into the air, and may be inhaled by the operator or absorbed through the skin. The liquid monomer is volatile, and may be inhaled in its gaseous state. In addition, the possibility of spillage of the liquid monomer is a constant threat to the operator. Moreover, upon combination of the powder and the liquid, a chemical reaction causes the immediate release of fumes, which may also be harmful to the operator if inhaled. In another example, epoxy resins are generally formed from two or more thick liquid components which are hand mixed on a benchtop, the process of which also releases potentially harmful vapors. In addition, as with virtually all commercially available uncured resins, mixed but uncured acrylic or epoxy material may be harmful and irritating if contacted with skin.

Moreover, conventional molding systems further cause an economic disadvantage to operators in that the flasks and attendant equipment used for each type of material are different. For instance, traditional flasks and injector modules for forming heat-curable appliances are different than traditional flasks and injector modules used for forming microwave-curable appliances. Thus, operators must purchase entirely separate equipment if they are to have the desired freedom to use both types of materials.

Thus, there is a need for an improved dental injection molding system which minimizes inaccurately dimensioned appliances, which protects operators from exposure to potentially dangerous fumes and chemicals and which allows operators the freedom to use at least some of the same equipment with more than one type of material.

As will become apparent from a detailed reading of the description, the system of the invention offers significant advantages over the prior art systems described above, most significantly including a system for pressurized and continuous injection in a closed system even during curing, which greatly minimizes the risk of inaccurately formed or nonuniform appliances. In addition, the injection system of the invention can accommodate conduction heat and microwave curing, both under pressure and without pressure. Lastly, use of the dispensing system of the invention will minimize operator exposure to harmful fumes and chemicals, regardless of the chemistry used to make the material. Other objects and advantages of the present invention will become obvious to the reader and it is intended that these objects and advantages are within the scope of the present invention.

SUMMARY OF THE INVENTION

It is an object of the invention to provide a pressurized dental injection molding system whereby material may be continuously pressurized in a mold up to the point of cure of the material.

It is a further object of the invention to provide a system for making injection molded dental appliances that can compensate for shrinkage or overfilling or underfilling.

It is also an object of the invention to provide a system for making injection molded dental appliances which at least partly vents the injector module and flask during injection.

It is yet another object of the present invention to provide an injection module for making injection molded dental appliances that may be used with both conduction heating and microwave curable material.

It is still another object of the present invention to provide a dispensing system that minimizes operator exposure to chemicals and vapors.

The invention includes a system and method for making injection molded dental appliance apparatuses having an injector module removably attached to a dental flask, a press and a controlled compression means, wherein the press and compression means introduce pressure into the dental flask and the injector module, which pressure may or may not be maintained during curing of the appliance. The invention also includes a system for dispensing dental appliance chemicals having at least one chemical dispensing apparatus and a bag; whereby a separate dispensing apparatus is used for each chemical and the chemicals are dispensed directly into the bag and mixed in the bag.

DETAILED DESCRIPTION OF THE PREFERRED EMBODIMENTS

Figure 1:
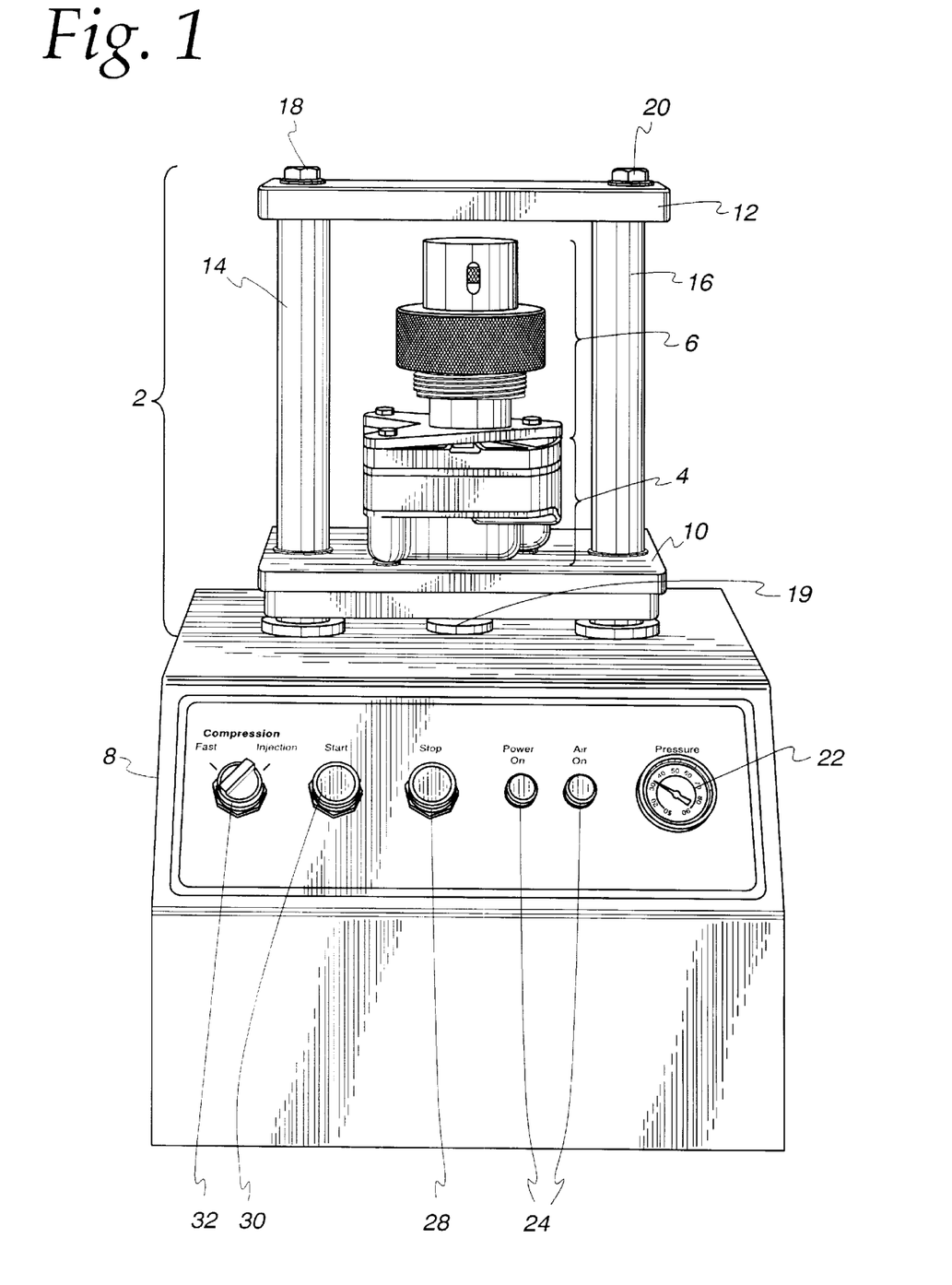
FIG. 1 is a schematic view of a dental injection molding system apparatus made in accordance with the principles of the invention, featuring a press, an assembled flask, an injector module and a compression device.

FIG. 1 illustrates a preferred embodiment of an injection molding system made in accordance with the principles of the present invention. The system includes a press 2, a compression device 8, a flask 4, and an injector module 6.

The press 2 includes a vertically moveable platform 10, a compression plate 12, and opposing first 14 and second 16 vertical platform posts running from the underside of compression plate 12 through platform 10 to compression device 8. The compression plate 12 is bolted to the platform posts 14 and 16 respectively by first and second bolting means 18 and 20. A press piston 19 connected to the compression device allows the platform 10 to be raised or lowered along first 18 and second 20 platform posts.

The compression device of the preferred embodiment illustrated in FIG. 1 includes a controller means for controlling various factors, such as pressure, speed and time. The compression device further includes a plurality of switches and visual and audible indicators, including a pressure indicator 22, a cycle completion indicator 24, stop and start buttons (28 and 30 respectively) and a selector switch 32. The compression device 8 further contains a compression means that is housed within the compression device. The compression means may be any means of raising and lowering platform 10 with press piston 19, which means are known in the art and which include an electronic controller for controlling factors such as pressure and speed of injection.

Figure 2A:
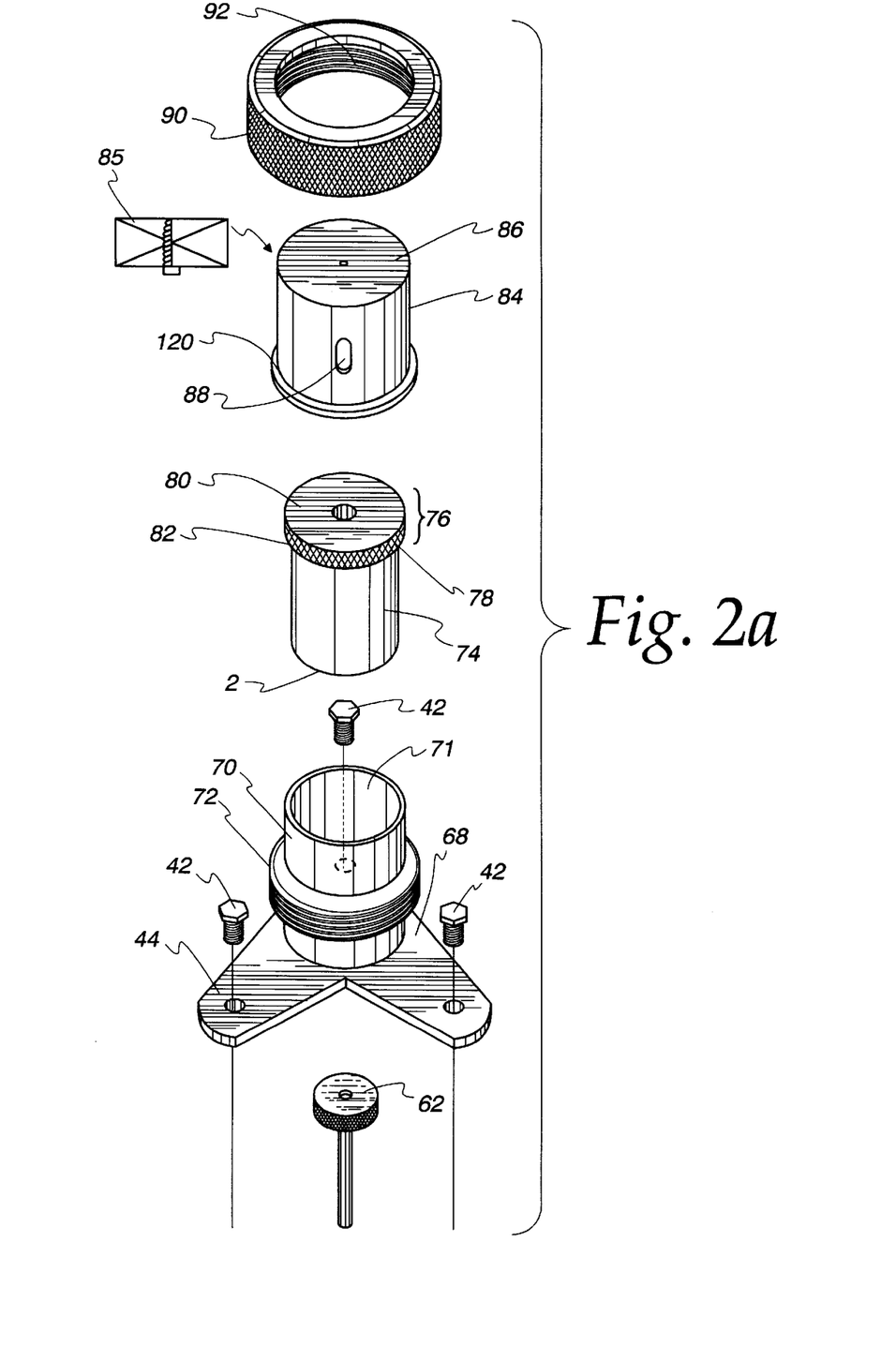
FIG. 2 is an exploded view of a flask and an injector module made according to the invention.
Figure 2B:
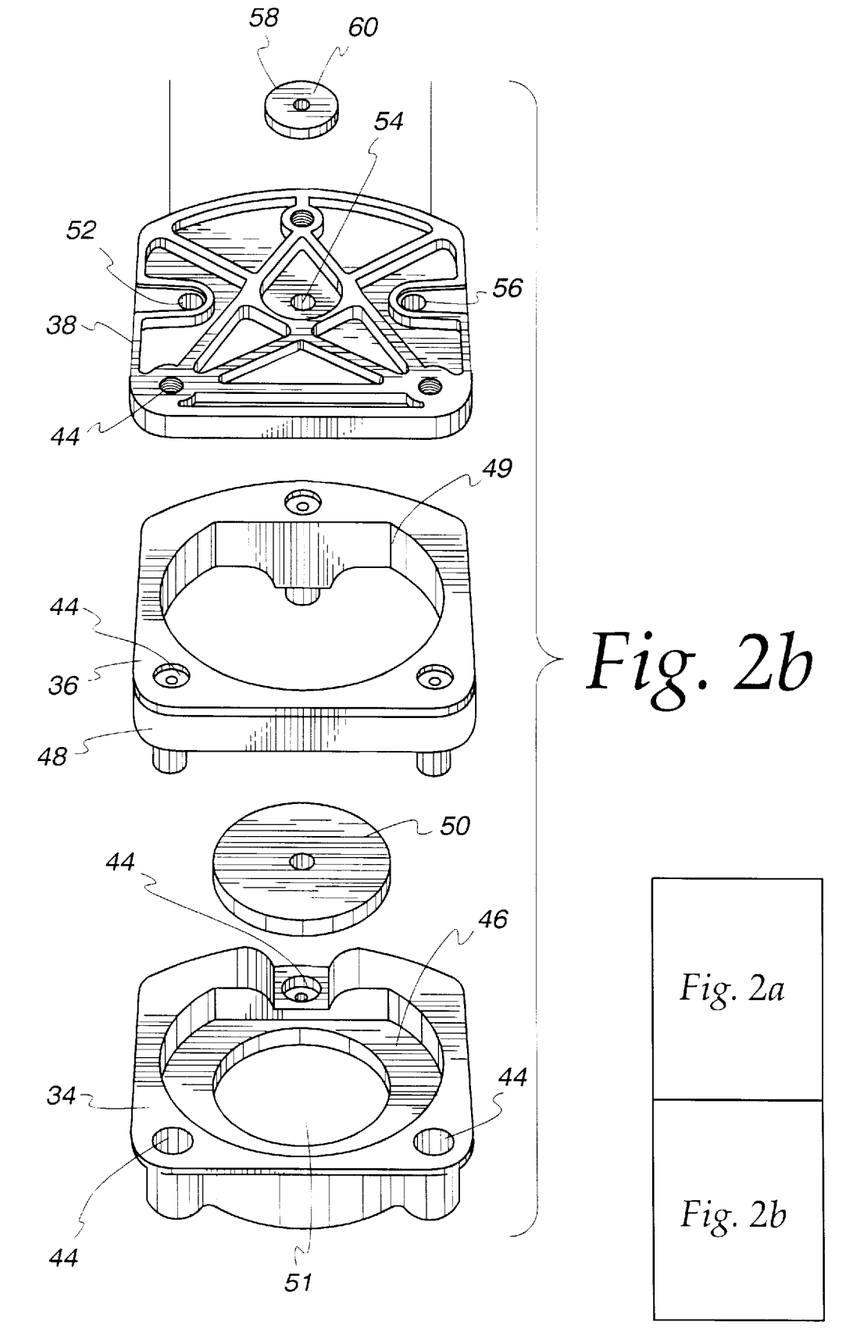
Figure 3:
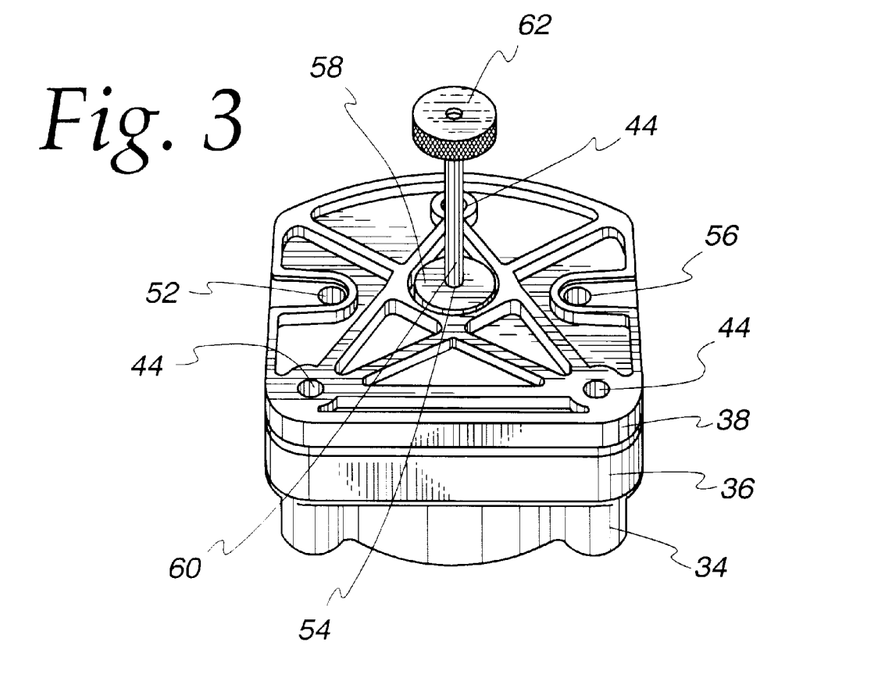
FIG. 3 is a schematic diagram of an assembled flask and sprue former of the invention.

FIGS. 1–3 illustrate a preferred embodiment of a microwavable flask 4 and injector module 6 of the invention, which flask 4 includes a bottom section 34, a center spacer section 36 and a top section 38, each section having a plurality of bolt holes 44 through which a plurality of bolts 42 are inserted upon assembly of the flask sections.

The bottom section 34 also includes a knockout plate 50, which fits into opening 51 and assists in separation of the sections upon completion of the method of the invention. Impressed into bottom section 34 is a bottom cavity 46 in which a cast and wax-up is inserted. The cast and wax-up and methods of their making are well known to practitioners of the art, and all of those methods are suitable for use with the dental flask and injector module of the invention.

The center spacer section 36 includes a spacer plate having an outer edge 48 and an inner edge 49, wherein the outer edge is shaped to be in registry with the outer edge of bottom 34 and top 38 sections, and the inner edge is shaped to be in registry with the edges of the bottom cavity 46 of the bottom section.

The top section 38 includes two vent openings 52 and 56, and one sprue former opening 54, into which a bushing 58 is inserted, although the number of vents, sprue former openings and bushings may vary in other embodiments of the invention. When the flask sections are assembled in registry with one another as illustrated in FIGS. 2b and 3, each set of bolt holes 44 (one set in each of the three sections 34, 36 and 38) are in registry with one another. Although the embodiment illustrated here shows three bolt holes, other embodiments with more or less than three bolt holes in dental flask 4 are contemplated to be within the scope of this invention. The bushing 58 includes an opening 60, which fits into sprue former opening 54. In another embodiment, the top section includes a top plate for use with pressureless curing The top plate includes a slide valve (not shown) that is closed when curing without the injector module is desired by the operator. The dental flask illustrated in FIG. 2 is constructed from material which is microwave conducting and which can withstand injection pressures of at least 3000 lbs. Other embodiments of the flask of the invention include a flask for use with conduction heating which can withstand injection pressures of at least 3000 lbs. and which is compatible with the injection methods of the invention.

The injector module 6 (used to inject the curable material into the appliance mold within the flask) is then assembled and attached to the reassembled flask 4. In the preferred embodiment of a microwavable flask 4 and injector module 6 as illustrated in FIG. 2a, the injector module 6 includes a plate 68, upon which is mounted a tubular injection cylinder 70 having a cavity 71 and with a plurality of bolt holes 44 in registry with those previously described. The injection cylinder 70 and plate 68 further have an injection orifice (not shown) which is constructed to be in alignment with the sprue opening in the dental flask. Disposed about the outside of the injection cylinder is a threaded pressure retaining band 72. The injection cylinder cavity 71 is designed to accommodate a solid cylindrical piston 74, having a piston cap 76 with a patterned exterior edge ridge 78, and top 80 and bottom 82 surfaces. This piston 74 is fitted to be removably inserted into the injection cylinder cavity 71 up to the bottom surface 82 of the piston cap 76. The injection cylinder 70 may further includes a tubular pressure cap 84 with a substantially flat cover 86, which includes a spring mechanism 85 and pressure retaining ring 90 which is threaded on the interior surface 92 to be compatible with the pressure retaining band 72 on the injection cylinder 70. The pressure cap 84 and the pressure retaining ring are used for curing under pressure, as illustrated in FIG. 2. At least one view hole 88 disposed in the side wall of the pressure cap 84. Disposed about the exterior surface of the pressure cap 84 is a pressure retaining ring 90. In another embodiment of the injector module used for pressureless curing, no pressure cap or pressure retaining ring are used. In the embodiments described herein, the injector module is constructed of a metal which does not conduct microwaves. The universal metal injector is a novel feature of the invention which may be used to inject material into both microwave flasks and conduction heating flasks, and may be used for pressured or pressureless curing. If used with pressure cap 84, the injector module applies continuous pressure and venting of the material during injection and either microwave or conduction heat cure, and holds the material in the injector in an uncured state while exposed to microwaves.

One preferred method of using the injection system to make molded dental appliances includes the steps of assembling the dental flask, creating an investment, or mold, for the desired appliance, attaching the injector module, preparing the curable material, injecting the curable material into the flask using the compression device of the invention, curing the curable material under pressure or without pressure, disassembling the flask and finally releasing the finished appliance.

The dental flask of the preferred embodiment illustrated in FIGS. 1–3 and 5–7 is assembled by first inserting knockout plate 50 into the bottom section 34 of dental flask 4. Investment material is then prepared according to known methods and placed into the cavity 46 of the bottom section 34. A cast and wax-up which have been formed in accordance with methods well known in the art are positioned in the assembled bottom cavity 46 of the bottom section 34. The center section 36 is then positioned upon the bottom section 34 such that the bolt holes 44 in each of the two sections are in registry. Additional investment material is then added to the flask on top of the cast and wax-up.

Figure 5:
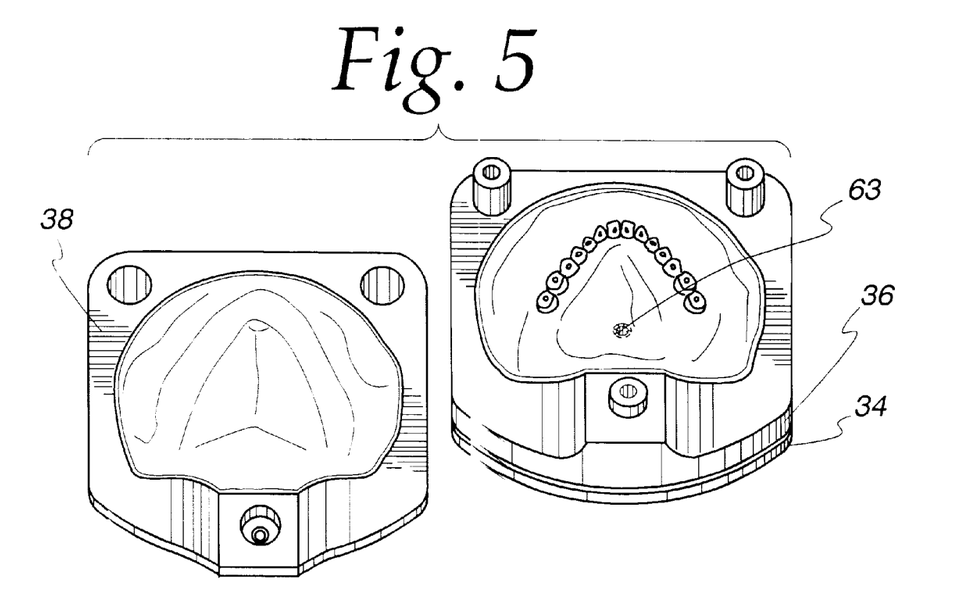
FIG. 5 shows a separated flask of the invention containing a formed mold for an appliance made in accordance with the principles of the invention.

Once the flask is filled with investment material, the flask is reassembled. The reassambled flask may include either a top section for use with continuous pressurized injection during curing, or it may be reassembled with a top section for pressureless curing, as described above. The top section 38 is then positioned such that the bolt holes 44 of the top section are in registry with the bolt holes 44 of the bottom and center sections (34 and 36 respectively). Bolts 42 which extend from the top section into the bottom section of the flask are then inserted into the bolt holes and hand tightened. Vent openings 52 and 56 allow excess investment to be released from the assembled flask upon tightening of the bolts 42, which vent openings 52 and 56 subsequently become sealed by solidification of the investment material. Prior to the hardening of the investment, the sprue former 62 is then positioned in the sprue former opening 54 such that the sprue former contacts the wax-up, thus forming the passage 63 in the investment material through which curable material is injected (as illustrated in FIG. 5). Once the investment is hardened, the sprue former 62 is removed. The cast and wax -up in the invested flask is then heated for a time sufficient to soften the wax. The top section 38 then separated from the bottom 34 and center 36 sections and the wax is removed, leaving a cavity in the investment as shown in FIG. 5. This cavity forms the mold for the appliance which is subsequently filled with uncured material as described below. The flask sections are then reassembled but not bolted.

In order to attach injector module 6 to reassembled flask 4, the plate 68 with injection cylinder 70 is aligned with dental flask 4 so that bolt holes 44 in plate 68 are in registry with bolt holes 44 in dental flask 4. The bolts 42 are then inserted into bolt holes 44 and hand tightened. The bolts are then tightened using press 2 and compression device 8 of the invention. This step involves placing the dental flask 4 with attached plate 68 and injection cylinder 70 on platform 10 so that the cavity 71 of the injection cylinder 70 is facing the lower surface of the compression plate 12. The various controls on the compression device 8 are then used to raise the platform 10 and compress the flask so that the bolts 42 may be tightened. Once platform 10 stops rising, bolts 42 are tightened, and platform 10 is lowered.

Figure 6:
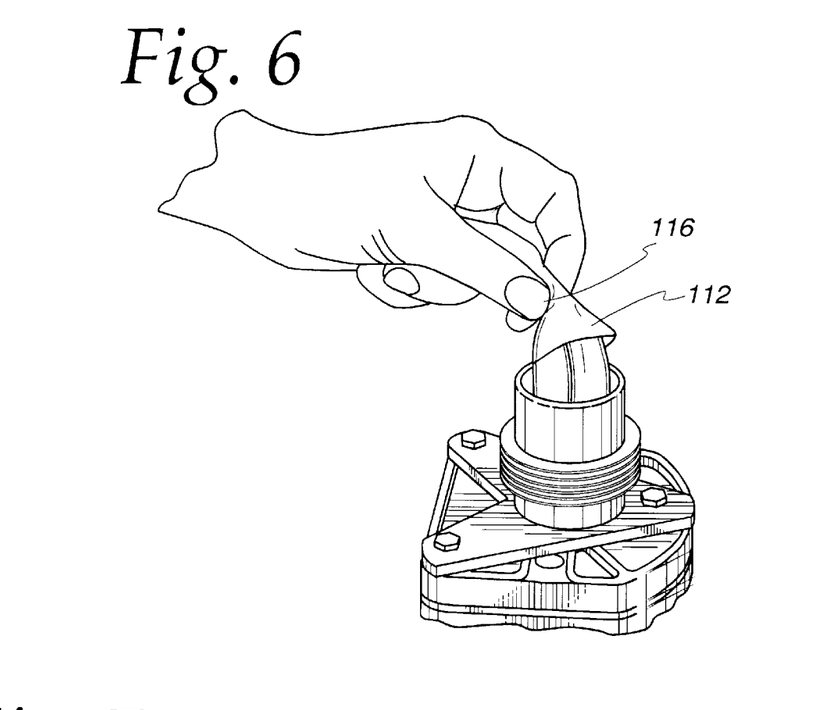
FIG. 6 shows insertion of appliance material into an injector module of the invention.

Once the dental flask 4 and injection cylinder 6 are assembled and bolted together as described above, the material may be prepared using the dispensing system of the invention. The dispensing system illustrated in FIG. 4 depicts preparation of an acrylic resin material, and includes a powder dispenser 98 with lever 100, a cup 102, a funnel 104, a funnel stand 106, a stopper 108, a liquid dispenser 110 with a lever 116, and a container 96, such as the bag illustrated in the preferred embodiment shown in FIGS. 4d–4f. The dispensing system may also include an umbrella 112, as shown in FIG. 6, which may be used to seal the container 96. The container 96 may be any container which will not degrade when filled with the material, which is capable of being closed and which is thin enough to allow the operator to assess through touch the consistence of the material.

Figure 4A:
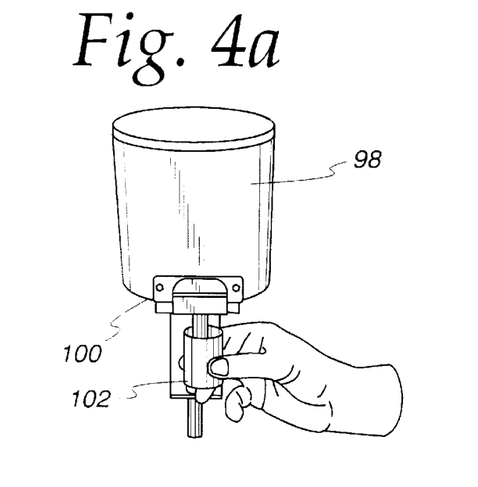
FIG. 4 depicts the material dispensing system of the invention.
Figure 4B:
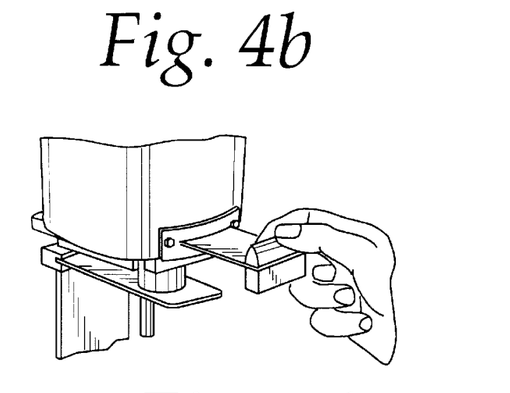
Figure 4C:
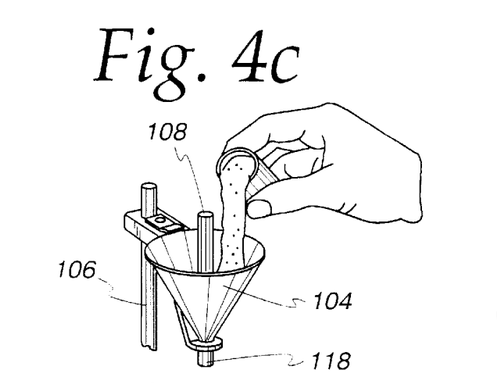
Figure 4D:
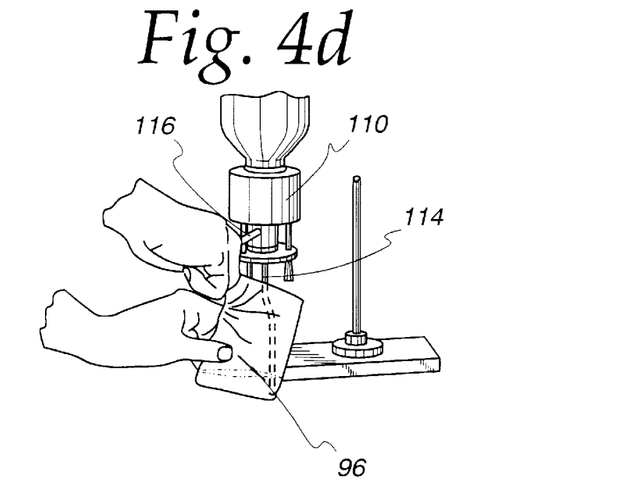
Figure 4E:
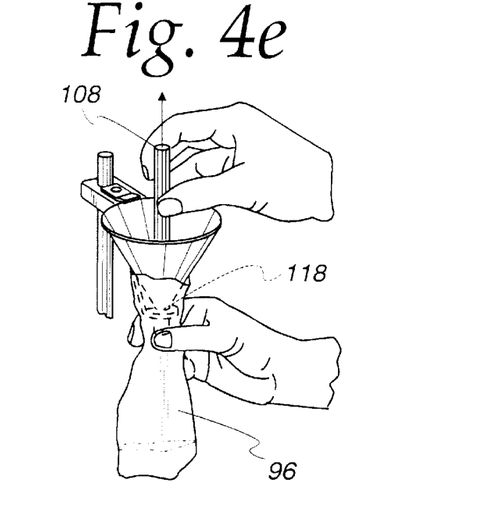
Figure 4F:
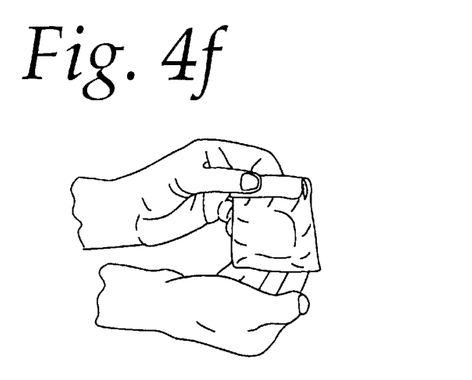

The powder dispenser lever 100 is used to dispense a measured amount of polymer powder into the cup 102. (FIGS. 4a and b). The powder is then poured into funnel 104, a spout 118 of which is blocked by the stopper 108, and which funnel 104 is held upright by use of the funnel stand 106 (FIG. 4c). The container 96 is then disposed around a nozzle 114 of the liquid dispenser 110, and an appropriate amount of liquid monomer is then dispensed into container 96 by movement of lever 116 (FIG. 4d). The container 96 containing the liquid monomer is placed below funnel spout 118 and stopper 108 is removed, causing powder to flow into container 96 (FIG. 4e). The top portion of the filled container 96 is then closed and the contents gently mixed by hand (FIG. 4f). The use of the material dispensing apparatus and the method described above minimizes aerosolized powder and exposure to potentially harmful vapors, and reduces the risk of operator exposure to potentially harmful chemicals and vapors. This particular embodiment illustrates preparation of an acrylic resin compound, but it is understood that any powder/liquid or liquid/liquid combination may be used with the dispensing apparatus of the invention, provided the material resulting from the mixed components is sufficiently viscous for use with the mold and injector module of the invention.

Once the container 96 containing the material is prepared, the filled container 96 is placed into the injection cylinder cavity 71 such that the empty top of container 96 extends out of the top of the injection cylinder 70. If an umbrella 112 is used, the top of the container 96 may then be threaded through an opening 116 in the umbrella 112 and the umbrella 112 pushed down until it reaches the material, as shown in FIG. 6, with the empty top of the container 96 extending through the opening 116 of umbrella 112. The top of the container is then folded and the filled container 96 is inserted into the cavity 71 of the injection cylinder 70. The injector piston 74 is then inserted into the injection cylinder cavity 71, thus compressing the filled container 96.

If the continuous pressure embodiment of the injector module is used, the pressure cap 84 is placed over the piston 74, with the piston cap ridge 78 visible through the pressure cap view hole 88. The pressure retaining ring 90 is then disposed around the piston cap 76, with the interior surface 92 of the ring 90 removably resting upon the lower rim 120 of the pressure cap.

In yet another embodiment of the system, the dispensing system may not be used and the material may be loaded directly into the injector module without use of a container.

The assembled dental flask 4 and filled injector module 6 are then placed on platform 10 of press 2 so that in the pressureless embodiment, the top of piston 74 is facing the lower surface of the compression plate 12, and in the pressured embodiment, the top of pressure cap 86 is facing the lower surface of the compression plate 12. The compression device is then activated to cause injection of the material into the investment through the injection orifice in the injector module, by pressure applied to the injector module 6 and dental flask 4. In the continuous pressure embodiment of the invention, once the injection is substantially completed, the pressure retaining ring 90 is tightened about the pressure retaining band 72, thus causing spring mechanism 85 to exert pressure on the piston 74, which creates pressure in the dental flask 4. Upon completion of injection, the flask and injector module are removed from the press.

Figure 7:
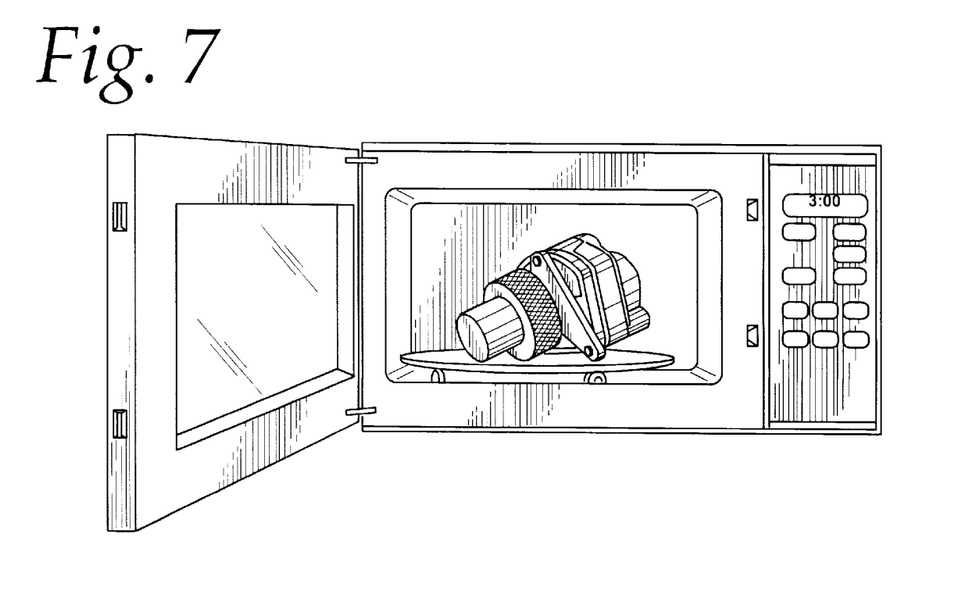
FIG. 7 illustrates the continuous injection apparatus of the invention whereby the appliance is microwave cured under continuous pressure.

The pressurized dental flask 4 with attached injector module 6 is then cured, for instance by microwave as shown in FIG. 7. Until the point of cure (hardening) of the material, the pressure in the dental flask 4 allows for continued injection of uncured material at a constant pressure as necessary to fill void spaces within the investment without causing overfilling of the investment. In addition, the continuous pressure exerted on the appliance minimizes distortion of the appliance due to shrinkage during polymerization, or cure, of the material.

In the pressureless injection system of the invention, the injection of material into the flask is as described above, but after injection, the slide valve on the top section of the flask is closed to seal the material within the flask, and the injector module 6 is removed. The flask is then cured as described above.

After cure, the dental flask 4 is cooled. In the pressurized embodiment, the pressure retaining ring 90, pressure cap 86, piston 74 and bag 96 are removed from the injection cylinder 70 prior to cooling. The cured appliance is removed and finished in the conventional manner.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be within the scope of the claims.

What is claimed is:

1. A system for mg injection molded dental appliance apparatuses using a curable material, the system comprising:
    a dental flask;
    a pressure cap including spring mean and pressure retaining means, the spring means adapted to removably engage the pressure cap;
    a metal injector module adapted to sealably receive the pressure cap and removably attached to the dental flask, the metal injector including an injection cylinder, a piston and a spring mechanism, the injection cylinder adapted to removably receive the piston;
    a press adapted to removably apply a force to the pressure cap; and
    compression means;
    wherein the press and the compression means introduce pressure into the dental flask;
    which the dental flask with the attached metal injector is adapted to be positioned in a microwave oven such that curing of the curable material in the dental flask is effected;
    wherein the pressure cap provides continuous pressure to the dental flask during the curing; and
    wherein the metal injector provides continuous injection of the curable material to the dental flask during the curing.

2. The system according to claim 1 wherein the dental flask comprises:
    a bottom section further comprising a cavity;
    a center section comprising a spacer plate having an inner edge and an outer edge, wherein the inner edge is shaped to be in registry with the walls of the cavity; and
    a top section comprising a sprue former opening and at least one vent means.

3. The system of claim 1 wherein the compression means further comprises an electronic controller.

4. The system of claim 3 wherein the electronic controller controls pressure, time and speed of injection.

5. The system of claim 1 wherein the injector module does not transmit microwaves.

6. The system of claim 1 wherein the dental flask is not pressurized during curing.

7. The system of claim 1 wherein the injector module and dental flask are pressurized during curing.

8. The system of claim 7 wherein the injector module is capable of injecting material into the dental flask during curing.

9. The system of claim 1 wherein the pressure retaining means is a pressure retaining ring and wherein the injection cylinder further comprises a pressure retaining band which removably engages the pressure retaining ring.

10. The dental flask according to claim 1 wherein the dental flask is microwavable.

11. The dental flask according to claim 1 wherein the dental flask is conduction heatable.

12. A system for making injection molded dental appliance apparatuses comprising:
    a dental flask;
    a metal injector module removably attached to the dental flask; wherein the injector module further comprises:
    an injector cylinder;
    piston;
    a spring mechanism;
    a pressure cap having a spring mechanism, the spring means adapted to removably engage the pressure cap, the pressure cap adapted to sealably attach to the injector module; and
    a pressure retaining means;
    wherein the pressure retaining means is adapted to removably engage the pressure cap and wherein the piston is adapted to be removably inserted into the injection cylinder;
    wherein the pressure cap is adapted to removably receive a force from a compression means; and
    wherein the dental flask with the attached metal injector is adapted to be positioned in a microwave oven.

* * * * *

UNITED STATES PATENT AND TRADEMARK OFFICE
CERTIFICATE OF CORRECTION

PATENT NO.    : 6,186,761
DATED         : February 13, 2001
INVENTOR(S)   : Petkow et al.

It is certified that error appears in the above-identified patent and that said Letters Patent is hereby corrected as shown below:

Column 7, Line 48, delete "mg" and substitute --making-- therefor;

Column 8, Line 50, delete "mechanism" and substitute --means-- therefor

Signed and Sealed this

Fifth Day of June, 2001

*Attest:*

*Attesting Officer*

NICHOLAS P. GODICI
*Acting Director of the United States Patent and Trademark Office*